(12) United States Patent
Weiss

(10) Patent No.: US 7,214,748 B2
(45) Date of Patent: May 8, 2007

(54) PROCESS FOR THE PRODUCTION OF AN AZO-CATALYST FOR THE POLYMERIZATION OF OLEFINS

(75) Inventor: Thomas Weiss, Mannheim (DE)

(73) Assignee: Lanxess Deutschland GmbH, Leverkusen (DE)

( * ) Notice: Subject to any disclaimer, the term of this patent is extended or adjusted under 35 U.S.C. 154(b) by 243 days.

(21) Appl. No.: 10/793,512

(22) Filed: Mar. 4, 2004

(65) Prior Publication Data

US 2004/0181018 A1 Sep. 16, 2004

(30) Foreign Application Priority Data

Mar. 10, 2003 (DE) ................................ 103 10 289

(51) Int. Cl.
*C08F 4/60* (2006.01)
*C07F 15/00* (2006.01)
*C07F 15/04* (2006.01)

(52) U.S. Cl. ................... 526/169.1; 526/134; 526/161; 526/165; 526/172; 502/103; 502/104; 502/167; 556/138

(58) Field of Classification Search ................ 502/103, 502/104, 167; 556/138; 526/134, 161, 165, 526/169.1, 172
See application file for complete search history.

(56) References Cited

U.S. PATENT DOCUMENTS

| | | | | |
|---|---|---|---|---|
| 5,175,326 | A | 12/1992 | Klabunde | 556/138 |
| 6,410,664 | B1 | 6/2002 | Bansleben et al. | 526/141 |
| 6,506,704 | B1 | 1/2003 | Bansleben et al. | 502/155 |
| 6,506,861 | B2 | 1/2003 | Wang et al. | 526/172 |
| 6,541,585 | B2 | 4/2003 | Johnson et al. | 526/161 |
| 6,573,345 | B1 | 6/2003 | Bansleben et al. | 526/161 |
| 6,576,779 | B1 | 6/2003 | Bansleben et al. | 556/413 |
| 6,613,915 | B1 | 9/2003 | Johnson et al. | 548/402 |
| 2002/0028741 | A1 | 3/2002 | Wang et al. | 502/103 |
| 2002/0028897 | A1 | 3/2002 | Johnson et al. | 526/319 |
| 2002/0032289 | A1 | 3/2002 | Wang et al. | 526/171 |
| 2002/0037982 | A1 | 3/2002 | Johnson et al. | 526/172 |
| 2002/0099155 | A1 | 7/2002 | Inoue et al. | 526/172 |
| 2003/0130449 | A1 | 7/2003 | Wang et al. | 526/134 |
| 2003/0130453 | A1 | 7/2003 | Wang et al. | 526/172 |
| 2004/0030072 | A1 | 2/2004 | Kristen et al. | 526/172 |

FOREIGN PATENT DOCUMENTS

| | | |
|---|---|---|
| DE | 1 232 747 | 1/1967 |
| DE | 199 61 340 | 7/2001 |
| EP | 0 990 664 | 4/2000 |
| EP | 1 238 989 | 9/2002 |
| WO | 2004/020478 | 3/2004 |

OTHER PUBLICATIONS

Angew. Chem., 113, (month unavailable), 2001, pp. 550-557, Stefan Mecking, "Olefin-Polymerisation durch Komplexe später Ubergangsmetalle—ein Wegbereiter der Ziegler-Katalysatoren erscheint in neuem Gewand".
Chem. Rev., 100, (month unavailable) 2000, pp. 1169-1203, Steven D. Ittel and Lynda K. Johnson, "Late-Metal Catalysts for Ethylene Homo- and Copolymerization".
Chem. Rev., 100, (month unavailable) 2000, pp. 1479-1493, Lisa S. Boffa and Bruce M. Novak, "Copolymerization of Polar Monomers with Olefins Using Transition-Metal Complexes".
Angew. Chem., 99, (month unavailable) 1987, pp. 76-77, Von K. Alexander Ostoja Starzewski & Josef Witte, "Steuerung des Molekulargewichts von Polyethen bei der Synthese mit Bis(ylid)nickel-Katalysatoren".
J. Mot. Catal., 41, (month unavailable) 1987, pp. 123-134, Ulrich Klabunde and Steven D. Ittel, "Nickel Catalysis for Ethylene Homo- and Co-Polymerization".
Macromolecules, 35, Jul. 30, 2002, pp. 6071-6073, Dirk L. Schröder, Wilhelm Keim, Martin A. Zuideveld, and Stefan Mecking, "Ethylene Polymerization by Novel, Easily Accessible Catalysts Based on Nickel(II) Diazene Complexes".

*Primary Examiner*—Caixia Lu
(74) *Attorney, Agent, or Firm*—Nicanor A. Kohncke

(57) ABSTRACT

The present invention relates to a process for the production of a catalyst by reacting metal compounds with azo ligands, the catalyst, the use of this catalyst as a polymerization catalyst, a process for olefin (co)polymerization with the aid of these catalysts, reaction products of these catalysts with co-catalysts, the olefin (co)polymer, the use of this olefin (co)polymer for the production of molded parts and also molded parts produced from the olefin (co)catalyst.

11 Claims, No Drawings

PROCESS FOR THE PRODUCTION OF AN AZO-CATALYST FOR THE POLYMERIZATION OF OLEFINS

FIELD OF THE INVENTION

The present invention relates to a process for the production of a catalyst by reacting metal compounds with azo ligands, the catalyst, the use of these catalysts as polymerization catalysts, a process for olefin (co)polymerization with the aid of these catalysts, reaction products of these catalysts with co-catalysts, the olefin (co)polymer, the use of the olefin (co)polymer for the production of molded parts and also molded parts produced from the olefin (co)polymers.

BACKGROUND OF THE INVENTION

There is a great need for catalyst compounds that are suitable for polymerization of olefins in the presence of polar additives.

The polyolefin industry works with processes that polymerize ethylene as well as other non-polar 1-olefins with the aid of various catalysts and radical initiator systems. These polymerizations can be carried out using organometallic Ziegler-Natta coordination catalysts, chromium catalysts and most recently metallocene-type compounds of early transition metals, as well as radical initiators. Furthermore, it has been found that these catalysts react very sensitively to a number of substances that impair or entirely prevent catalytic activity. For example, it is known that traces of oxygen, carbon monoxide, water or oxygen-containing organic compounds, which act as donors, can deactivate these catalysts. If these substances are present, the use of catalysts is normally limited to radical initiator systems.

To improve these circumstances and also to copolymerize polar monomers, catalysts based on late transition metals were developed. Summary articles can be found in Mecking, S. *Angew. Chem.* 2001, 113, 550; Ittel, S.: Johnson, L. K. and Brookhart M. *Chem. Rev.* 2000, 100, 1169 and Boffa, L. S.; Novak, B. M in *Chem. Rev.* 2000, 100, 1479.

Typically, the complex types used are divided into those with anionic ligand structures or those with neutral ligand structures. The group of complexes with an anionic ligand structure shows particularly robust properties with regard to the above-mentioned catalyst, as a result of the uncharged (neutral) active polymerization species. This is a result of the low Lewis acidity of the catalytic species. Current research interest is therefore focused precisely on these catalyst types. Thus in *J. Angew. Chem.* 1987, 99, 76, Ostoja Starzewski and K. A. Witte disclosed such catalysts with a [P,O]-ligand type. Klabunde, U.; Ittel, S. D. report of similar catalysts in *J. Mol. Catal.* 1987, 41, 123. Comparable catalysts [P,O] complexes are disclosed also in U.S. Pat. No. 5,175,326.

A new catalyst class A, similar in conception to [P,O]-complexes, was developed which, instead of the phosphorus donor, has an iminic nitrogen donor.

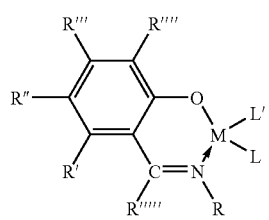

A

Large steric groups R and R'''', which screen off the apical positions around the metal centre as far as possible are a common feature.

The corresponding processes for the production of such catalysts are disclosed in more detail in WO 98/30609, WO 98/42664, WO/98/42665, DE-A 199 61 340, WO 00/56785, WO 01/92347 and WO 02/08236.

Surprisingly, it was found that special azo dyes can also be inserted into the series of anionic ligand systems for complexing. Azo dyes represent a class of compounds that have already been thoroughly investigated, and that can also be synthesized on an industrial scale.

In *Macromolecules,* 2002, 35, 6071, von Schröder, D. L.; Keim, W.; Zuideveld, M. A.; Mecking, S. disclose this kind of ligand for the production of single-site catalysts for the polymerization of olefins. However, activation with the widest variety of Lewis acids in the presence of polar additives and sterically demanding ortho-substituted compounds, which have an influence on activity and molar mass, are not disclosed.

EP-A 1 170 308 discloses ligands that also have an azo-function but, in contrast to the present invention, have no oxygen-metal bond, but an amide-like nitrogen-metal bond. Nor are transition metal compounds with late transition elements disclosed. No sterically demanding substituents in ortho positions to amide-like nitrogen in such complexes are disclosed.

DE 1 232 747 B2 discloses a monometallic, chelating azo ligand, which in addition to the azo donor function, has a metal-carbon (phenyl) bond, in other words a carbanionic phenyl-metal bond rather than an oxygen-metal bond. As metal-phenyl bonds of nickel are demonstrably polymerization-active, the complex postulated in DE 1 232 747 B2 would not effect a chelate-like coordination of the metal centre during polymerization. A disadvantage of this process is therefore the change in the geometry of the metal complex during polymerization. Thus good results cannot be expected with regard to polymer uniformity.

The present invention provides catalysts that allow olefin (co)polymerization in the presence of polar additives.

SUMMARY OF THE INVENTION

The present invention includes a process for the production of a catalyst including
a) dissolution of compounds of the general formula (I)

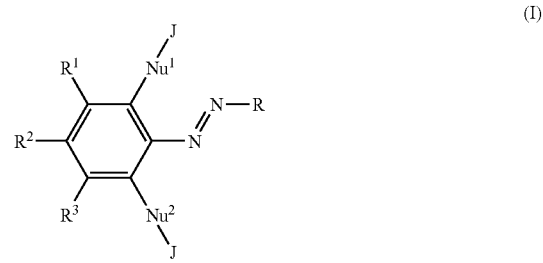

in an aprotic non-polar solvent, wherein
$Nu^1$, $Nu^2$ independently of each other, stand for —O, —S, —Se, —$PR^2$, —$NR^a$, —COO groups
where
$R^a$ stands for hydrogen, substituted or unsubstituted alkyl- or aryl groups and
J stands for an element selected from the $1^{st}$ or $2^{nd}$ main group of the periodic table R, $R^1$, $R^2$, and $R^3$ are the same or different groups, which are selected, independently of each other, from the group consisting of H, halogens, substituted or unsubstituted $C_1$–$C_8$ alkyl-, $C_2$–$C_8$ alkenyl-, $C_3$–$C_{12}$ cycloalkyl-, $C_7$–$C_{13}$ aralkyl- and $C_6$–$C_{14}$ aryl groups and $R^1$ can form a ring with $R^2$ or $R^3$ and $R^2$ can form a ring with $R^3$, b) dissolution of a metal compound of the general formula (II)

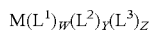  (II)

in an aprotic non-polar solvent,
wherein
M stands for an element of the $4^{th}$ to $12^{th}$ sub-group of the periodic table,
$L^1$ is a neutral ligand,
$L^2$, $L^3$ independently of each other are an anionic ligand, wherein $L^1$ and/or $L^2$ with $L^3$ can be linked to each other by one or more covalent bonds and
W can be an integer from 0 to 3,
Y can be an integer from 0 to 3 and
Z can be an integer from 0 to 3, wherein if one of the three variables W, Y or Z=0, the sum of the two remaining variables is equal to 2, 3 or 4.

c) mixing of solutions a) and b).

DETAILED DESCRIPTION OF THE PRESENT INVENTION

The process according to the present invention includes reacting compounds of formula (I),
wherein
$Nu^1$ and $Nu^2$ are —O,
J stands for an element of the $1^{st}$ main group of the periodic table
R is selected from the group consisting of substituted or unsubstituted $C_6$–$C_{14}$ aralkyl groups
$R^1$, $R^2$ and $R^3$ are the same or different groups and independently of each other are selected from the group consisting of H, substituted or unsubstituted $C_1$–$C_8$ alkyl groups, $C_2$–$C_8$ alkylene groups, $C_3$–$C_{12}$ cycloalkyl groups, $C_7$–$C_{13}$ aralkyl groups, $C_6$–$C_{14}$ aryl groups,
with compounds of formula (II),
wherein
M is selected from the group consisting of Ti, Zr, Hf, Cr, V, Fe, Co, Ni, Ru, Rh, Pd, Os, Ir, Pt, Cu, Ag, Au, Zn, Cd and Hg
$L^1$ is an organic or inorganic neutral ligand, selected from the group consisting of phosphanes of the general formula $(R^{13})_xPH_{3-x}$, amines with the general formula $(R^{13})_xNH_{3-x}$, tetraalkyl ethylene diamines, tetraaryl ethylene diamines, ethers with the general formula $(R^{13})_2O$, alcohols with the general formula $(R^{13})OH$, pyridine derivatives with the general formula $C_5H_{5-x}(R^{13})_xN$, CO, $C_1$–$C_{12}$ alkyl nitrile, $C_6$–$C_{14}$ aryl nitrile and mono- or polyethylenically unsaturated double bond systems,
wherein
$R^{13}$ is selected from the group consisting of H, $C_1$–$C_8$ alkyl groups, benzyl groups and $C_6$–$C_{14}$ aryl groups and
x stands for an integer from 0 to 3, and
$L^2$, $L^3$ is an anionic ligand, selected from the group consisting of halide ions, amide anions of the formula $R^{14}R^{15}N$, $C_1$–$C_6$-alkyl anions, allyl anions, methallyl anions, benzyl anions and aryl anions, wherein
$R^{14}$ and $R^{15}$ independently of each other are selected from the group consisting of H, $C_1$–$C_8$ alkyl groups, benzyl groups and $C_6$–$C_{14}$ aryl groups and $R^{14}$ can also be covalently linked to $R^{15}$ and
W is an integer from 0 to 3
Y is an integer from 0 to 3 and
Z can be an integer from 0 to 3, wherein if one of the three variables W, Y or Z=0, the sum of the two remaining variables is equal to 2, 3 or 4.

The process according to the present invention also includes reacting compounds of formula (I),
wherein
$Nu^1$ and $Nu^2$ are O
J is lithium or hydrogen
R is mesityl, 2,4,6-trimethyl phenyl or 2,6-diisopropyl phenyl,
$R^1$, $R^2$ and $R^3$ are the same or different groups and are selected, independently of each other, from the group consisting of H, $C_1$–$C_8$ alkyl groups and $C_6$–$C_{14}$ aryl groups,
with compounds of formula (II),
wherein
M is selected from the group consisting of Ti, Zr, Cr, V, Fe, Co, Ni, Pd, Cu and Zn
$L^1$ is a neutral ligand, selected from the group consisting of triphenyl phosphine, triethyl phosphine, trimethyl phosphine, trimethyl phosphane, dibenzophosphol, triphenyl phosphite, triethyl phosphite, trimethyl phosphite, triphenyl phosphite, tetramethyl ethylene diamine, trimethyl amine, triethyl amine, dimethyl aniline, diethyl aniline, benzyl dimethyl amine, benzyl diethyl amine, diisopropyl amine, diethyl amine, dimethyl amine, diphenyl amine, phenylene diamine, diethyl ether, tetrahydrofuran, water, methanol, ethanol, pyridine, 2-picoline, 3-picoline, 4-picoline, 2,3-lutidine, 2,4-lutidine, 2,5-lutidine, 2,6-lutidine, 3,5-lutidine, CO, acrylonitrile, acetonitrile, propionitrile, butyronitrile, benzonitrile, ethenyl, propenyl, cis-2-butenyl, trans-2-butenyl, cyclohexenyl and norbornenyl,
$L^1$, $L^3$ is an anionic ligand, selected from the group consisting of chloride, bromide, dimethyl amide, diethyl amide, amide, 2-carboxylic acid ester metallyl, allyl, methyl, ethyl, n-propyl, i-propyl, n-butyl, tert-butyl, hexyl and phenyl,
W is an integer from 0 to 3
Y is an integer from 0 to 3
Z can be an integer from 1 to 3, wherein if one of the three variables W, Y or Z=0, the sum of the two remaining variables is equal to 2,3or4.

The process according to the present invention further includes reacting compounds of formula (I)
wherein
$Nu^1$ and $Nu^2$ are –O,
J is lithium, hydrogen
R is mesityl or 2,6-diisopropyl phenyl
$R^1$ is tert-butyl or phenyl
$R^2$ is H
$R^3$ is tert-butyl
with compounds of formula (II), wherein
M is Ni or Pd
$L^1$ is tetramethylene diamine, triphenyl phosphane, trimethyl phosphane or 1,5-cyclooctadiene
$L^2$ is chloride, phenyl or methyl
$L^3$ is chloride, phenyl or methyl
W is an integer from 0 to 3
Y is an integer from 0 to 3

Z is an integer from 0 to 3, wherein if one of the three variables W, Y or Z=0, the sum of the two remaining variables is equal to 2, 3 or 4.

The present invention further provides catalysts that can be obtained by the process according to the present invention.

The present invention further provides the use of the catalyst that can be obtained by the process according to the present invention as a polymerization catalyst.

The present invention further provides a process for the production of olefin (co)polymers, wherein a catalyst that is obtained by the process according to the present invention, is reacted in the presence of olefinic monomers selected from the group consisting of 1-olefins, cycloolefins, functionalized 1-olefins and mixtures of these.

Boron or aluminum compounds can be added as co-catalysts to the reaction mixture in the process for the production of olefin (co)polymers.

A molar ratio of co-catalyst to metal M in the compound of formula (II) in the range of 1:10 to 1:10000 can be used in the process for the production of olefin (co)polymers.

Aluminum oxanes can be used as co-catalysts in the process for the production of olefin (co)polymers.

The process for the production of olefin (co)polymers can be carried out in polar solvents or solvent mixtures.

The present invention further provides reaction products that are obtained by reacting the catalyst from the process according to the present invention with the co-catalyst.

The present invention further provides olefin (co)polymers that can be obtained by the process for the production of olefin (co)polymers.

The present invention further provides the use of the olefin (co)polymers for the production of molded parts of all kinds.

The present invention further provides the molded parts that can be obtained from the olefin (co)polymer.

Compounds of formula (I)

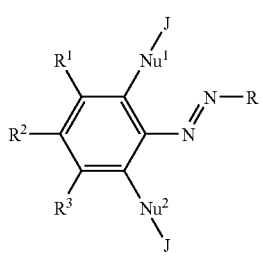

are used for the process according to the present invention, wherein $Nu^1$, $Nu^2$ independently are selected from the group consisting of —O, —S, —Se, —$PR^a$, —$NR^a$, or —COO groups and $R^a$ stands for hydrogen, alkyl- or aryl groups. O, $NR^a$ and COO groups are preferably used for $Nu^1$. More preferably, $Nu^1$ stands for oxygen.

The group J stands here for an element from the $1^{st}$ or $2^{nd}$ main groups of the periodic table. H, Na, Li, Mg, Ca are preferably used for J, more preferably Li and H.

Here, R, $R^1$, $R^2$ and $R^3$ are the same or different groups, which are selected independently of each other from the group consisting of H, halogens, substituted or unsubstituted $C_1$–$C_8$ alkyl-, substituted or unsubstituted $C_2$–$C_8$ alkenyl-, substituted or unsubstituted $C_3$–$C_{12}$ cycloalkyl-, substituted or unsubstituted $C_7$–$C_{13}$ aralkyl- and substituted or unsubstituted $C_6$–$C_{14}$ aryl groups, substituted or unsubstituted nitro groups and $R^1$ can form a ring with $R^2$ or $R^3$ and $R^2$ can form a ring with $R^3$.

R, $R^1$, $R^2$ and $R^3$ can all be halogens such as fluorine, chlorine, bromine and iodine. Fluorine and chlorine are preferred.

R, $R^1$, $R^2$ and $R^3$ can all be substituted or unsubstituted alkyl groups that contain the above-mentioned number of C atoms in the basic chain. Preferred unsubstituted alkyl groups include methyl, ethyl, n-propyl, iso-propyl, n-butyl, iso-butyl, sec-butyl, tert-butyl, n-pentyl, iso-pentyl, sec-pentyl, neo-pentyl, 1,2-dimethyl propyl, iso-amyl, n-hexyl, iso-hexyl, sec-hexyl, n-heptyl, iso-heptyl and n-octyl. $C_1$–$C_6$-alkyl groups such as methyl, ethyl, n-propyl, iso-propyl, n-butyl, iso-butyl, sec-butyl, tert-butyl, n-pentyl, iso-pentyl, sec-pentyl, neo-pentyl, 1,2-dimethyl-propyl, iso-amyl, n-hexyl, iso-hexyl, sec-hexyl are preferred. $C_1$–$C_4$ alkyl groups such as methyl, ethyl, n-propyl, iso-propyl, n-butyl, iso-butyl, sec-butyl and tert-butyl are more preferred, and these groups can each bear one or more other substituents. Other preferred substituents include all halogen atoms, fluorine, chlorine and bromine being preferred. Suitable examples include, fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl are preferred. Fluoromethyl, difluoromethyl, trifluoromethyl and perfluorobutyl are more preferred.

R, $R^1$, $R^2$ and $R^3$ can all be substituted or unsubstituted alkenyl groups that contain the above-mentioned number of C atoms in the basic chain. Preferred unsubstituted alkenyl groups include alkenyl groups having one to four isolated or conjugated double bonds. Vinyl, 1-allyl, 3-allyl, ω-butenyl, ω-pentenyl, ω-hexenyl, 1-cis-buta-1,3-dienyl and 1-cis-hexa-1,5-dienyl are preferred and these groups can each bear further substituents. Preferred substituted alkenyl groups include isopropenyl, 1-isopropenyl, α-styryl, β-styryl, 1-cis-1,2-phenyl ethenyl and 1-trans-1,2-phenyl ethenyl.

R, $R^1$, $R^2$ and $R^3$ can all be substituted or unsubstituted cycloalkyl groups that contain the above-mentioned number of C atoms in the ring. Preferred unsubstituted cycloalkyls are cyclopropyl, cyclobutyl, cyclopentyl, cyclohexyl, cycloheptyl, cyclooctyl, cyclononyl, cyclodecyl, cycloundecyl and cyclododecyl. Cyclopentyl, cyclohexyl and cycloheptyl are more preferred. The cycloalkyls can bear further substituents. Preferred substituted cycloalkyl groups include 2-methyl cyclopentyl, 3-methyl cyclopentyl, cis-2,4-dimethyl cyclopentyl, trans-2,4-dimethyl cyclopentyl, cis-2,5-dimethyl cyclopentyl, trans-2,5-dimethyl cyclopentyl, 2,2,5,5-tetra-ethyl cyclopentyl, 2-methyl cyclohexyl, 3-methyl cyclohexyl, 4-methyl cyclohexyl, cis-2,6-dimethyl cyclohexyl, trans-2,6-dimethyl cyclohexyl, cis-2,6-diisopropyl cyclohexyl, trans-2,6-diisopropyl cyclohexyl, 2,2,6,6-tetramethyl cyclohexyl, 2-methoxy cyclopentyl, 2-methoxy cyclohexyl, 3-methoxy cyclopentyl, 3-methoxy cyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 32-chloro-cyclohexyl, 4-chlorocyclohexyl, 2,5-dichlorocyclohexyl, 2,2,6,6-tetrachloro-cyclohexyl, 2-thiomethyl cyclopentyl, 2-thiomethyl cyclohexyl, 3-thiomethyl cyclopentyl and 3-thiomethyl cyclohexyl.

R, $R^1$, $R^2$ and $R^3$ can all be substituted or unsubstituted aralkyl groups that contain the above-mentioned number of C atoms along the main chain. Preferred unsubstituted aralkyl groups include $C_7$ to $C_{12}$ phenyl alkyl such as benzyl, 1-phenethyl, 2-phenethyl, 1-phenyl-propyl, 2-phenyl-propyl, 3-phenyl-propyl neophyl (1-methyl-1-phenylethyl), 1-phenyl-butyl, 2-phenyl-butyl, 3-phenyl-butyl and 4-phenyl-butyl. Benzyl is more preferred. The substituents for the aralkyl groups are alkyl-, aryl-, aralkyl-, alkoxy-, aryloxy-, aralkyloxy-, dialkylamino-, halogen-, keto and hydroxyl.

R, $R^1$, $R^2$ and $R^3$ can all be substituted or unsubstituted aryl groups that have the above-mentioned number of C atoms within the ring. Preferred unsubstituted aryl groups include phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl. Phenyl, 1-naphthyl and 2-naphthyl are more preferred. Phenyl is most preferred. These aryl groups can bear further substituents.

The substituted alkyl-, alkenyl-, cycloalkyl-, aralkyl- and aryl groups include not only the substituents already preferred but also:

Substituted and/or unsubstituted $C_1$–$C_8$-alkyl groups such as methyl, ethyl, n-propyl, iso-propyl, n-butyl, iso-butyl, sec-butyl, tert-butyl, n-pentyl, iso-pentyl, sec-pentyl, neo-pentyl, 2,3-dimethyl-propyl, iso-amyl, n-hexyl, iso-hexyl, sec-hexyl, n-heptyl, iso-heptyl and n-octyl. $C_1$–$C_6$-alkyl are preferred, $C_1$–$C_4$-alkyl such as methyl, ethyl, n-propyl, iso-propyl, n-butyl, iso-butyl, sec-butyl and tert-butyl are more preferred. The substituted $C_1$–$C_8$-alkyl groups are understood to include mono- or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl. Fluoromethyl, difluoromethyl, trifluoromethyl and perfluorobutyl are preferred.

$C_3$–$C_{12}$-cycloalkyl such as cyclopropyl, cyclobutyl, cyclopentyl, cyclohexyl, cyclohepty, cyclooctyl, cyclononyl, cyclodecyl, cycloundecyl and cyclododecyl. Cyclopentyl, cyclohexyl and cycloheptyl are preferred.

$C_7$–$C_{13}$-aralkyl, $C_7$–$C_{12}$ phenyl alkyl such as benzyl, 1-phenethyl, 2-phenethyl, 1-phenyl-propyl, 2-phenyl-propyl, 3-phenyl-propyl, neophyl (1-methyl-1-phenyl-ethyl), 1-phenyl-butyl, 2-phenyl-butyl, 3-phenyl-butyl and 4-phenyl-butyl being preferred. Benzyl is more preferred.

$C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl. Phenyl, 1-naphthyl and 2-naphthyl are preferred. Phenyl is more preferred.

One or more halogens selected independently of each other such as fluorine, chlorine, bromine or iodine. Fluorine and/or chlorine are preferred.

Nitro and/or nitroso groups. Nitro is preferred.

$C_1$–$C_6$-alkoxy groups such as methoxy, ethoxy, n-propoxy, iso-propoxy, n-butoxy, iso-butoxy, sec-butoxy, tert-butoxy, n-pentoxy, iso-pentoxy, n-hexoxy and iso-hexoxy. Methoxy, ethoxy, n-propoxy and n-butoxy are preferred.

$C_6$–$C_{14}$-aryloxy groups such as phenoxy, ortho-cresyloxy, meta-cresyloxy, para-cresyloxy, α-naphthoxy, β-naphthoxy or 9-anthryloxy.

Silyl groups of the general formula $SiR^{10}R^{11}R^{12}$, wherein $R^{10}$, $R^{11}$ and $R^{12}$ are selected independently of each other from the group consisting of hydrogen, $C_1$–$C_8$-alkyl groups, benzyl groups and $C_6$–$C_{14}$-aryl groups. The trimethyl silyl-, triethyl silyl-, triisopropyl silyl-, diethyl isopropyl silyl-, dimethyl thexyl silyl-, tert-butyl dimethyl silyl-, tert-butyl diphenyl silyl-, tribenzyl silyl-, triphenyl silyl- and the tri-para-xylyl silyl groups are preferred. The trimethyl silyl group and the tert-butyl dimethyl silyl group are more preferred.

Silyloxy groups $OSiR^{10}R^{11}R^{12}$, wherein $R^{10}R^{11}$ and $R^{12}$ are selected independently of each other from the group consisting of hydrogen, $C_1$–$C_8$-alkyl groups, benzyl groups and $C_6$–$C_{14}$-aryl groups. The trimethyl silyloxy-, triethyl silyloxy-, triisopropyl silyloxy-, diethyl-isopropyl silyloxy-, dimethyl thexyl silyloxy-, tert-butyl dimethyl silyloxy-, tert-butyl diphenyl silyloxy-, tribenzyl silyloxy-, triphenyl silyloxy- and the tri-para-xylyl silyloxy group are preferred. The trimethyl silyloxy group and the tert-butyl dimethyl silyloxy group are more preferred.

Five- to six-link nitrogen-containing heteroaryl groups such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl. These five- and six-link nitrogen-containing heteroaryl groups may contain other substituents such as $C_1$–$C_8$-alkyl groups. Methyl, ethyl, n-propyl, iso-propyl, n-butyl, iso-butyl, sec-butyl, tert-butyl, n-pentyl, iso-pentyl, sec-pentyl, neo-pentyl, 1,2-dimethylpropyl, iso-amyl, n-hexyl, iso-hexyl, sec-hexyl, n-heptyl, iso-heptyl and n-octyl are preferred here. $C_1$–$C_6$-alkyl groups are more preferred. $C_1$–$C_4$-alkyl groups such as methyl, ethyl, n-propyl, iso-propyl, n-butyl, iso-butyl, sec-butyl and tert-butyl are most preferred. These $C_1$–$C_8$-alkyl groups can also bear further substituents on the heteroaryl groups. These include:

Halogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl. Fluoromethyl, difluoromethyl, trifluoromethyl and perfluorobutyl are preferred.

$C_3$–$C_{12}$-cycloalkyls such as cyclopropyl, cyclobutyl, cyclopentyl, cyclohexyl, cycloheptyl, cyclooctyl, cyclononyl, cyclodecyl, cycloundecyl and cyclododecyl. Cyclopentyl, cycohexyl and cycloheptyl are preferred;

$C_7$–$C_{13}$-aralkyls. $C_7$–$C_{12}$-phenyl alkyls such as benzyl, 1-phenethyl, 2-phenethyl, 1-phenyl-propyl, 2-phenyl-propyl, 3-phenyl-propyl, neophyl (1-methyl-1-phenyl ethyl), 1-phenyl-butyl, 2-phenyl-butyl, 3-phenyl-butyl and 4-phenyl-butyl are preferred. Benzyl is most preferred.

$C_6$–$C_{14}$-aryls. Phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl are preferred. Phenyl, 1-naphthyl and 2-naphthyl are more preferred. Phenyl is most preferred.

Halogens such as fluorine, chlorine, bromine or iodine. Fluorine and chlorine are preferred.

$C_1$–$C_6$-alkoxy groups such as methoxy, ethoxy, n-propoxy, iso-propoxy, n-butoxy, iso-butoxy, sec-butoxy, tert-butoxy, n-pentoxy, iso-pentoxy, n-hexoxy and iso-hexoxy. Methoxy, ethoxy, n-propoxy and n-butoxy are preferred.

$C_6$–$C_{14}$-aryloxy groups such as phenoxy, ortho-cresyloxy, meta-cresyloxy, para-cresyloxy, α-naphthoxy, β-naphthoxy or 9-anthryloxy.

Silyl groups $SiR^{10}OR^{11}R^{12}$, wherein $R^{10}$, $R^{11}$ and $R^{12}$ are selected independently of each other from the group consisting of hydrogen, $C_1$–$C_8$-alkyl groups, benzyl groups and $C_6$–$C_{14}$ aryl groups. The trimethyl silyl-, triethyl silyl-, triisopropyl silyl-, diethyl isopropyl silyl-, dimethyl thexyl silyl-, tert-butyl dimethyl silyl-, tert-butyl diphenyl silyl-, tribenzyl silyl-, triphenyl silyl- and the tri-para-xylyl silyl group are preferred. The trimethyl silyl group and the tert-butyl dimethyl silyl group are more preferred.

Silyloxy groups $OSiR^{10}R^{11}R^{12}$, wherein $R^{10}$, $R^{11}$ and $R^{12}$ are selected independently of each other from the group consisting of hydrogen, $C_1$–$C_8$-alkyl groups, benzyl groups and $C_6$–$C_{14}$ aryl groups. The trimethyl silyloxy-, triethyl silyloxy-, triisopropyl silyloxy-, diethyl isopropyl silyloxy-, dimethyl thexyl silyloxy-, tert-butyl dimethyl silyloxy-, tert-butyl diphenyl silyloxy-, tribenzyl silyloxy-, triphenyl silyloxy- and the tri-para-xylyl silyloxy group are preferred. The trimethyl silyloxy group and the tert-butyl dimethyl silyloxy group are more preferred.

Preferably the group R is selected from the group consisting of mesityl, 2,4,6-trimethyl phenyl or 2,6-diisopropyl phenyl. R is preferably mesityl or 2,6-diisopropyl phenyl. The groups $R^1$ and $R^3$ are preferably selected from the group consisting of H, $C_1$–$C_8$-alkylene, $C_6$–$C_{14}$ arylene, substituted or unsubstituted nitro groups, fluorine and chlorine. $R^1$ and $R^3$ are preferably selected from the group consisting of tert-butyl and phenyl. $R^2$ is preferably hydrogen.

Groups $R^1$ to $R^3$ can each be linked to each other to form a 5 to 12-link ring. Thus, —(CH$_2$)$_3$— (trimethylene), —(CH$_2$)$_4$— (tetramethylene), —(CH$_2$)$_5$— (pentamethylene), —(CH$_2$)$_6$— (hexamethylene), —CH$_2$—CH=CH—, —CH$_2$—CH=CH—CH$_2$—, —CH=CH—CH=CH—, —O—CH$_2$—O—, —O—CHMe-O—, —O—CH—(C$_6$H$_5$)—O—, —O—CH$_2$—CH$_2$—O—, —O—CMe$_2$-O—, —NMe-CH$_2$—CH$_2$—NMe-, —NMe-CH$_2$ NMe- or —O—SiMe$_2$-O— where Me=CH$_3$ bridges can be introduced at the positions of $R^1$ and $R^2$ and also $R^1$ and $R^3$ and $R^2$ and $R^3$.

The central atom M of the compound (II) is preferably selected from the group consisting of elements from the 4$^{th}$ to 12$^{th}$ sub group of the periodic table. The elements Ti, Zr, Hf, Cr, V, Fe, Co, Ni, Ru, Rh, Pd, Os, Ir, Pt, Cu, Ag, Au, Zn, Cd and Hg are preferred. Ti, Zr, Cr, V, Fe, Co, Ni, Pd, Cu and Zn are more preferred. Ni and Pd are most preferred.

The group $L^1$ is a neutral ligand. Neutral ligands include all neutral ligands known to the person skilled in the art. Organic or inorganic neutral ligands selected from the group consisting of phosphanes of the general formula $(R^{13})_xPH_{3-x}$, amines with the general formula $(R^{13})_xNH_{3-x}$, ethers with the general formula $(R^{13})_2O$, alcohols with the general formula $(R^{13})OH$, pyridine derivatives with the general formula $C_5H_{5-x}(R^{13})_xN$, CO, $C_1$–$C_{12}$ alkyl nitriles, $C_6$–$C_{14}$ aryl nitriles and mono- or polyethylenically unsaturated double bond systems are preferred.

The group $R^{13}$ for the general formula of the phosphanes, amines, ethers, alcohols and pyridine derivatives is selected from the group consisting of H, $C_1$–$C_8$ alkyl groups, benzyl groups and $C_6$–$C_{14}$ aryl groups. The definition of $C_1$–$C_8$ alkyl groups and $C_6$–$C_{14}$ aryl groups is to be understood to include all substituted and unsubstituted alkyl- and aryl groups as well as their preferred ranges, which have already been defined for the groups R, $R^1$, $R^2$ and $R^3$ in the relevant range of the number of C atoms. The index x stands for an integer from 0 to 3. For the phosphanes and amines, x is preferably 3, for the pyridine derivatives x is preferably 0 or 1.

Preferred phosphanes for the group $L^1$ include triphenyl phosphane, perfluoro triphenyl phosphane, trimethyl phosphane, triethyl phosphane, dibenzo phosphol, tricyclohexyl phosphane. Preferred amines include trimethyl amine, triethyl amine; dimethyl benzyl amine. Preferred ethers include diethyl ether, tetra-hydrofuran and water. Preferred alcohols include methanol, ethanol, and isopropanol. Preferred pyridine derivatives include pyridine 2-picoline, 3-picoline, 4-picoline, 2,3-lutidine, 2,5-lutidine, 2,6-lutidine, 3,5-lutidine. Preferred alkyl nitriles include acetonitrile, propionitrile as well as butyronitrile, malonic acid nitrile, oxalic acid nitrile, succinic acid nitrile, acrylic acid nitrile, fumaric acid nitrile, maleic acid nitrile. Preferred aryl nitrites include benzonitrile, 2-naphthyl nitrile, 1-naphthyl nitrile, terephthalic acid nitrile. Preferred ethylenically unsaturated double bond systems include ethenyl, propenyl, cis-2-butenyl, trans-2-butenyl, cyclohexenyl and norbornenyl.

Tetramethyl ethylene diamine, 1,5-cyclooctadienyl ligands ("COD"), triphenyl phosphane and acetonitrile are preferred as $L^1$.

The group $L^2$ is an anionic ligand that can optionally be linked to $L^1$ by one or more covalent bonds. An anionic ligand is understood to mean any anionic ligand known to the person skilled in the art. Anionic ligands selected from the group consisting of halide ions, amide ions of the general formula $R^{14}R^{15}N$, $C_1$–$C_6$ alkyl anions, allyl anions, methallyl anions, benzyl anions and aryl anions are preferred.

Groups $R^{14}$ and $R^{15}$ are selected independently of each other from the group consisting of H, $C_1$–$C_8$ alkyl groups, benzyl groups and $C_6$–$C_{14}$ aryl groups, and $R^{14}$ and $R^{15}$ can also be linked covalently. The definition of the $C_1$–$C_8$ alkyl groups and the $C_6$–$C_{14}$ aryl groups includes all substituted and/or unsubstituted alkyl groups and aryl groups and also their preferred ranges, which have already been defined for the groups R, $R^1$, $R^2$, $R^3$ and $R^4$ in the relevant range of the number of C atoms.

Preferred halide ions for the groups $L^2$ and $L^3$ include chloride and bromide. Preferred amide ions include amide, dimethyl amide, diethyl amide, diisopropyl amide, diphenyl amide, anilide, methyl phenyl amide. Preferred alkyl anions include methyl, ethyl, n-propyl, i-propyl, n-butyl, tert-butyl and hexyl. Preferred allyl anions include 1,3-aryl substituted allyl anions, 1,3-bistrimethylsilyl substituted allyl anions, preferably the parent compound $C_3H_5^-$. Anions of methacrylic acid ester 2-aryl substituted methallyl anions and the parent compound $C_4H_8^-$ include the preferred methallyl anions. The benzyl anion is also preferred. Phenyl is the preferred aryl anion.

Metal compounds of the general formula $M(L^1)_W(L^2)_Y(L^3)_Z$ include those in which the groups $L^1$ and/or $L^2$ with $L^3$ are linked to each other by a covalent bond. 1,5-cyclooctadienyl ligands ("COD"), 1,6-cyclodecenyl ligands or 1,5,9-all-trans-cyclododecatrienyl ligands are preferred.

$L^1$ can be tetramethyl ethylene diamine, only one nitrogen being coordinated with the M.

The indices W, Y and Z are, independently of each other, an integer from 0 to 3, wherein if W=0 the sum of Y and Z is 2,3 or 4. Preferably, W is 1 or 2 and Y and Z are 0 or 1.

In the process according to the present invention, compounds of formula (I) can be dissolved with metal compounds of formula (II) in the solvent known to the person skilled in the art. Preferred solvents include benzene, toluene, ethylbenzene, ortho-xylene, meta-xylene or para-xylene, chlorobenzene, cyclohexane, acetonitrile, tetrahydrofuran, methylene chloride or mixtures of these. The reaction is carried out in the temperature range known to the person skilled in the art. The reaction is preferably carried out in a temperature range of −100° C. to +150° C., particularly preferably in the range of −78° C. to +100° C. The reaction of the compounds of formula (I).with the metal compounds of formula (II) must take place with exclusion of oxygen and moisture.

The molar ratio of compound of formula (I) and M of formula (II) is in the range of 5:1 to 1:5, preferably in the range 1:1 to 1:3. Stoichiometric quantities are preferred.

For polymerization, it is necessary to produce the catalyst from the process according to the present invention separately in situ before polymerization. The compounds of formula (I) and the metal compounds of formula (II) can also be introduced into a reactor already charged with monomer and co-catalyst, so that the catalytically active species is formed first in situ during polymerization.

If $L^2$ in $M(L^1)_W(L^2)_Y$ is selected from the group of the $C_1$–$C_6$ alkyl groups, benzyl anions or aryl anions, the catalyst is preferably formed in situ before polymerization.

The compounds of the general formula (I) can be produced successfully in a two-stage reaction. In the first stage, aromatics of the general formula (III)

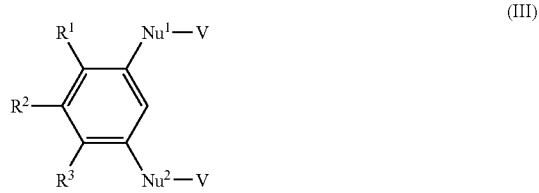

(III)

wherein
V stands for hydrogen, an alkali- or an earth alkali metal
are reacted with electrophilic aryl diazonium salts of the general formula (IV)

(IV)

in which the groups $Nu^1$, $Nu^2$, R, $R^1$, $R^2$, $R^3$ are as defined above and A- is an anion of strong acids selected from the group consisting of $F^-$, $Cl^-$, $Br^-$, $J^-$, $SO_4^{2-}$, $NO_3^-$, $ClO_4^-$, $ClO_3^-$, $CF_3COO^-$, $CF_3SO_3^-$, $BF_4^-$, $PF_6^-$, $B(C_6F_5)_4^-$ or anionic metalate complexes.

The compounds of the general formula (I) are generally produced in a second reaction from ligands of the general formula (III), in which the groups are as defined above. To synthesize the compounds of formula (I), the ligands of formula (III) are freed from group V with the aid of a strong base.

The metal alkyls known to the person skilled in the art can be used as bases. Methyl lithium, ethyl lithium, n-butyl lithium, sec-butyl lithium, tert-butyl lithium, hexyl lithium, Grignard compounds such as ethyl magnesium bromide, also lithium amide, sodium amide, potassium amide, potassium hydride or lithium diisopropyl amide ("LDA") are preferred. High-boiling solvents such as toluene, ortho-xylene, meta-xylene, para-xylene, ethyl benzene or mixtures of these are suitable solvents, as are non-cyclic or cyclic ethers such as 1,2-dimethoxy ethane, tetrahydrofuran or diethyl ether.

This removal of the group V is completed within a range of 1 min to 12 hours. A reaction time of 2 to 10 hours is preferred, 3 to 5 hours being preferred. During the reaction, the temperature is in the range of −196 to 0° C. A range of −90° C. to −20° C. is preferred. The ligands of formula (III) are metalated with exclusion of air and moisture.

All aprotic, polar or non-polar solvents known to the person skilled in the art can be used for the reaction of the ligands of formula (III) with the bases. Aprotic, polar solvents such as methylene chloride, acetonitrile, acrylonitrile, benzonitrile, tetrahydrofuran, diethyl ether or lutidine are preferred.

After reaction with the bases, the solvent can be removed from the product by the method known to the person skilled in the art. The metalated ligand obtained can be purified by the method known to the person skilled in the art. The preferred purification method is crystallization.

The production of diazonium salts is disclosed by a) Zollinger, H. in Chemie der Azofarbstoffe, 1958, Birckhäuser Verlag, b) by Hashida, Y., Landells, R. G. M., Lewis, G. E., Szele, I., Zollinger, H. in J. Am. Chem. Soc. 1978, 100, 2816, c) by Laali, K., Szele, I., Zollinger H., in Helv. Chim. Acta 1983, 66, 1737 and d) in Houben Weyl, Methoden in der Organischen Chemie, Volume X/3, p. 220 and is generally known to the person skilled in the art.

For diazotization, aromatic amines are reacted in the presence of Lewis or Bronstedt acids and nitrozating agents such as organic and inorganic nitrites. $BF_3$ has proved itself as a Lewis acid, $HBF_4$, sulfuric acid, HCl, HF as Bronstedt acids. The reaction time is 1 to 48 hours, preferably 1 to 15 hours. Both strong acids and protic polar solvents such as water, methanol or mixtures of these have proved to be preferred solvents for inorganic nitrites. However, when using organic nitrites such as iso-amyl nitrite, aprotic polar solvents such as tetrahydrofuran or esters, and methylene chloride, are preferred. The diazonium salts can be isolated with weakly-coordinating anions, such as $BF_4^-$, as slightly soluble solids.

The diazonium salts are then reacted with activated aromatics such as resorcinol derivatives, 1,3-dithiophenols, 1,3-(aralkyl-N,N')-phenylene diamines, 1,3-di-carboxy benzene derivatives. When phenols are used here, the corresponding alkali phenolates are first produced and the reaction is carried out in a slightly acid to alkaline pH range, preferably in the pH range 14 to 6. The azo compound formed is then purified by common methods such as filtration or phase separation. Further purification can then be carried out by column chromatography or crystallization using suitable solvents.

The catalysts that can be obtained by the process according to the present invention can be reacted with co-catalysts. Suitable co-catalysts are selected from the group consisting of aluminum- and/or boron compounds with electronic groups. Boron trifluoride, trispentafluoro phenyl borane, trispentafluoro phenyl aluminum, N,N-dimethyl anilinium-tetrakis-pentafluoro phenyl borate, tri-n-butylammonium-tetrakis-pentafluoro phenyl borate, N,N-dimethyl anilinium-tetrakis-(3,5-bisperfluoromethyl)-phenyl borate, tri-n-butylammonium-tetrakis-(3,5-bisperfluoro-methyl)-phenyl borate and also tritylium-tetrakispentafluoro phenyl borate. N,N-dimethyl anilinium-tetrakis-pentafluoro phenyl borate, tritylium-tetrakis pentafluoro phenyl borate and trispentafluoro phenyl borane are preferred.

If boron or aluminum compounds are used as co-catalysts for the catalysts from the process according to the present invention, they are generally used in a molar ratio of 1:10 to 10:1, in relation to M; preferably 1:2 to 5:1 and more preferably 1:1.5 to 1.5:1.

Another suitable class of co-catalysts is aluminoxanes.

The structure of the aluminoxanes is not precisely known. As disclosed in DE-A 3 007 725, they are products that are obtained by careful partial hydrolysis of aluminum alkyls. These products do not exist in pure form, but as mixtures of open-chain and cyclic structures of the type (V a) and (V b). These mixtures probably exist in a dynamic equilibrium to each other.

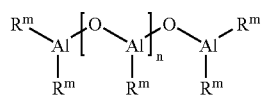
(Va)

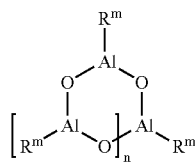
(Vb)

In formula (V a) and (V b), the groups $R^m$ are selected independently of each other from the group consisting of substituted or unsubstituted $C_1$–$C_{12}$ alkyl-, substituted or unsubstituted $C_3$–$C_{12}$ cycloalkyl, substituted or unsubstituted $C_7$–$C_{20}$ aralkyl, substituted or unsubstituted $C_6$ to $C_{14}$ aryl groups.

The $C_1$–$C_{12}$-alkyl groups are understood to be all alkyl groups with this number of C atoms in the main chain.

Preferred $C_1$–$C_{12}$-alkyl groups include methyl, ethyl, n-propyl, iso-propyl, n-butyl, iso-butyl, sec-butyl, tert-butyl, n-pentyl, iso-pentyl, sec-pentyl, neo-pentyl, 1,2-dimethylpropyl, iso-amyl, n-hexyl, iso-hexyl, sec-hexyl, n-heptyl, iso-heptyl, n-octyl, n-nonyl, n-decyl and n-dodecyl. $C_1$–$C_6$-alkyls such as methyl, ethyl, n-propyl, iso-propyl, n-butyl, iso-butyl, sec-butyl, tert-butyl, n-pentyl, iso-pentyl, sec-pentyl, neo-pentyl, 1,2-dimethylpropyl, iso-amyl, n-hexyl, iso-hexyl, sec-hexyl are more preferred. Methyl is most preferred.

The $C_3$–$C_{12}$ cycloalkyl groups are understood to include all cycloalkyl groups with this number of C atoms in the ring.

Preferred $C_3$–$C_{12}$ cycloalkyls are cyclopropyl, cyclobutyl, cyclopentyl, cyclohexyl, cycloheptyl, cyclooctyl, cyclononyl, cyclodecyl, cycloundecyl and cyclododecyl. Cyclopentyl, cyclohexyl and cycloheptyl are particularly preferred.

The $C_7$–$C_{20}$ aralkyl groups are understood to include all aralkyl groups with this number of C atoms in the basic skeleton.

$C_7$–$C_{20}$ aralkyls are preferred, $C_7$–$C_{12}$-phenylalkyl such as benzyl, 1-phenethyl, 2-phenethyl, 1-phenyl-propyl, 2-phenyl-propyl, 3-phenyl-propyl, 1-phenyl-butyl, 2-phenyl-butyl, 3-phenyl-butyl and 4-phenyl-butyl are more preferred. Benzyl is most preferred.

The $C_6$–$C_{14}$-aryl groups are understood to include all aryl groups with this number of C atoms in the ring. $C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl are preferred. Phenyl, 1-naphthyl and 2-naphthyl are more preferred. Phenyl is most preferred.

The parameter n in formula (V a) and (V b) stands for an integer from 0 to 40, preferably from 1 to 25, and more preferably from 2 to 22.

In Organometallics 1996, 15, 2213–26, Y. Koide, S. G. Bott, A. R. Barron also discuss cage-type structures for the aluminoxanes. A. R. Barron also reports on these structures in Macromol. Symp. 1995, 97, 15–25. Both the cage-type structures and the structures of formulae (V a) and (V b) are suitable as co-catalysts for the catalyst obtained by the process according to the present invention.

Mixtures of different aluminoxanes are preferred co-catalysts in cases in which polymerization takes place in a solution of a paraffin such as n-heptane or isododecane. A preferred mixture is CoMAO, which is commercially obtainable from Witco GmbH with a formula of

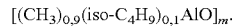
$[(CH_3)_{0.9}(iso\text{-}C_4H_9)_{0.1}AlO]_m$.

wherein m is 6 to 25.

To react the catalyst that is obtained from the process according to the present invention with aluminoxanes, an excess of aluminoxane in relation to M is generally needed. Useful molar ratios M:Al are in the range of 1:10, 1:10000, preferably 1:50 to 1:1000 and more preferably 1:100 to 1:500.

It is commonly thought that co-catalysts for the catalysts from the process according to the invention abstract a ligand $L^1$ or $L^2$. Instead of aluminum alkyl compounds of the general formula (V a) or (V b) or the aluminum- or boron compounds with electron-withdrawing groups disclosed above, the co-catalyst can also be olefin complexes of rhodium or nickel.

Preferred Ni-(olefin)-complexes, which are commercially obtainable from Aldrich, have the following general structure: nickel-(olefin)y-complexes where y=1,2,3 or 4. $Ni(C_2H_4)_3$, $Ni(1,5$-cyclooctadiene$)_2$ $(Ni(COD)_2)$, $Ni(1,6$-cyclo-decadiene$)_2$, or $Ni(1,5,9$-all-trans-cyclododecatriene$)_2$ are preferred. $Ni(COD)_2$ is more preferred.

Suitable rhodium-(olefin)-complexes include mixed ethylene/1,3-dicarbonyl complexes of rhodium such as rhodium-acetyl acetonate-ethylene Rh (acac) $(CH_2=CH_2)_2$, rhodium-benzoyl acetonate-ethylene Rh $(C_6H_5-CO-CH-CO-CH_3)$ $(CH_2=CH_2)$, or Rh $(C_6H_5-CO-CH-CO-C_6H_5)$ $(CH_2=CH_2)_2$. Rh (acac) $(CH_2=CH_2)_2$ is preferred. This compound can be synthesized according to R. Cramer in Inorg. Synth. 1974, 15, 14.

The ease of the starting reaction for polymerization depends decisively on the nature of the ligand $L^1$. Such ligands $L^1$ with labile coordinating properties are preferably compounds having an olefinic group through which the metal is complexed. Nitriles and compounds with ether functions are also suitable.

The catalyst obtainable from the process according to the present invention and the co-catalyst together form a reaction product that is active as a catalyst system in the polymerization.

The activity of the catalyst system according to the present invention can be increased by adding other aluminum alkyls of the general formula $Al(R^m)_3$ or aluminoxanes preferably when compounds of the general formula (V a) or (V b) or the aluminum- or boron compounds with electron-withdrawing groups mentioned above are used as co-catalysts; aluminum alkyls of the general formula $Al(R^m)_3$ or aluminoxanes can also be used as molar mass regulators. Another effective molar mass regulator is hydrogen. The molar mass can be regulated well through the reaction temperature and pressure. If a boron compound is to be used as disclosed above, the addition of an aluminum alkyl of the general formula $Al(R^m)_3$ is preferred.

It was found that the catalyst that can be obtained by the process according to the present invention is suitable for polymerizing olefins in the presence of polar additives such as esters, ethers and nitriles. It polymerizes and copolymerizes ethylene particularly well.

Pressure and temperature conditions during polymerization can be selected within broad limits. A pressure range of 0.5 bar to 4000 bar has proved to be preferred, 10 to 75 bar or high pressure conditions of 500 to 2500 bar being more preferred. A temperature range of 0 to 120° C. has proved to be preferred, 40 to 100° C. being more preferred and 50 to 85° C. being most preferred.

The following olefins are possible monomers: ethylene, propylene, n-butene, 1-pentene, 1-hexene, 1-octene, 1-decene or 1-undecene, propylene and ethylene being preferred and ethylene being more preferred.

α-olefins, styrene, isobutene, cyclopentene, cyclohexene, norbornene and norbornadiene are suitable as comonomers. 1-butene, 1-pentene, 1-hexene, 4-methyl-1-pentene, 1-octene, 1-decene or 1-undecane are preferred. The α-olefins are used in quantities of 0.1 to 20 mol. % in relation to the polymer obtained. α-olefin quantities in the range of 0.5 to 10 mol. % are preferred.

Hexane, heptane, toluene, ortho-xylene, meta-xylene, para-xylene, ethyl benzene and mixtures of these, diethyl ether, tetrahydrofuran, chlorobenzene, 1,3-dichlorobenzene, dichloromethane and, under high-pressure conditions, supercritical ethylene are used as solvents. Hexane, toluene, chlorobenzene and dichloromethane are preferred.

The catalyst that can be obtained by the process according to the present invention can be regulated during polymerization by hydrogen, i.e. the molecular weight of the polymers that can be obtained using the catalyst system can be reduced by adding hydrogen. If sufficient hydrogen is added, waxes are obtained, the required hydrogen concentration depending on the type of polymerization unit used.

The catalyst that can be obtained by the process according to the present invention can also be used together with one or more other polymerzation catalysts known per se. Thus it can be used together with Ziegler-Natta catalysts,
supported metallocene catalysts of the transition metals of the 4$^{th}$ to 6$^{th}$ sub-groups of the periodic table of elements.
catalysts of the late transition metals as disclosed in WO 96/23010
Fe— or Co-complexes with pyridyl diimine ligands, as disclosed in WO 98/27124,
and also chromium oxide catalysts according to Phillips.

Here it is possible, on the one hand, to mix different catalysts with each other and to dose them together or to use co-supported complexes on a joint support, but also to dose different catalysts separately at the same point or different points in the polymerization vessel.

The present invention further provides that the catalyst that can be obtained by the process according to the invention, such as a catalyst where M=Ni, is suitable for polymerization or copolymerization of 1-olefins, preferably ethylene, in the emulsion polymerization process.

In addition to other 1-olefins as comonomers, such as propene, 1-butene, 1-hexene, 1-octene or 1-decene, polar comonomers can also be incorporated with the aid of the catalyst system, 0.1 to 50 mol. % comonomer preferably being used. Preferred polar monomers include acrylates such as acrylic acid, acrylic acid methyl ester, acrylic acid ethyl ester, acrylic acid-(2-ethyl)-hexyl ester, acrylic acid-n-butyl ester or acrylic acid-tert-butyl ester;

acrylonitrile;

methacrylic acid, methacrylic acid methyl ester, methacrylic acid ethyl ester, methacrylic acid-n-butyl ester or methacrylic acid-tert-butyl ester;

vinyl carboxylates, vinyl acetate being preferred;

unsaturated dicarboxylic acids, maleic acid being more preferred;

unsaturated dicarboxylic acid derivatives, maleic acid anhydride and maleic acid alkyl imides such as maleic acid methyl imide being most preferred.

Terpolymers with at least 2 of the polar monomers listed above or a mixture of polar and non-polar monomers each in the molar range of 0.1 to 99.8 mol. % and ethylene can also be produced.

The polymer produced with the aid of the catalyst that can be obtained by the process according to the present invention can be processed by the possibilities known to the person skilled in the art such as injection molding, extrusion, foaming, to produce other molded articles.

EXAMPLES

All work was carried out by the trailing tube technique with exclusion of air and moisture in a purified argon atmosphere. The apparatus is thoroughly heated before use in an oil pump vacuum and rinsed with purified argon. The NMR tubes are also filled under argon.

The polymer viscosity was measured to ISO 1628-3. The molar masses were measured by GPC carried out according to DIN 55672.

All solvents used to carry out the reaction, including those used for purification by column chromatography, were free of water and atmospheric oxygen. Thin layer plates from Machery-Nagel coated with silica gel (Polygram® SIL G/UV$_{254}$) or aluminum oxide (Polygram® ALOX N/UV$_{254}$) were used for thin-layer chromatographic analysis of the reaction courses. The following sorbents were used for column chromatography:

Silica gel 60, grain size 40–60 μm, 230–400 mesh (ASTM) (Baker)

Kieselguhr, purified, calcined, Erg. B. 6 (Riedel-de Haën).

NMR spectra were recorded in deuterated solvents at 293 K. The chemical shift is given in ppm (parts per million).

$^1$H-NMR: Standard internal by solvent, CDCl$_3$ δ=7.26; C$_6$D$_6$ δ=7.16 rel. SiMe$_4$ (where SiMe$_4$ δ=0).

$^{13}$C{$^1$H}-NMR: Standard internal by solvent, CDCl$_3$ δ=77.0; C$_6$D$_6$ δ=128.0; rel. SiMe$_4$ (where SiMe$_4$ δ=0).

Illustration of the ligands according to the present invention:

General Diazotizing Procedure (Example 1.1 and 1.2)

The mesityl amine (45 mmol) and an HBF$_4$ solution diluted with 25 ml water (180 mmol, 23.5 ml of a 48% solution in water) were reacted at 0° C. NaNO$_2$ (45 mmol, 3.1 g) dissolved in 4 ml water was then added slowly drop by drop, until a visible reaction to the reaction mixture begins on iodine-potassium starch paper. After stirring for 5 min, the diazonium salt was added to a solution of the 1,3-dihydroxyaryl derivative (45 mmol) in a 2n NaOH solution (400 mmol). This was then stirred for a further 2 h at 0° C. and 150 ml toluene was added. Once phase separation was complete, 100 ml water and 20 ml 20% HCl was added to the organic phase and thoroughly intermixed. After renewed separation of the phases, they were washed twice with 50 ml water in each case and all volatile constituents were removed from the organic phase in a vacuum. The orange-red residue was then taken up in 60 ml pentane and filtered. The residue was then dried. Further product can be obtained from the filtrate by crystallization at −20° C.

The procedure for diazotizing with 2,6-diisopropyl aniline is typically as follows:

The ligands are obtained by a coupling reaction of the diazonium salt with the corresponding phenols. The diazonium salt was produced within 60 min by reacting the 2,6-diisopropyl aniline (20 mmol) with isoamyl nitrate (2.9 g, 3.4 ml, 25 mmol) and $BF_3*OEt_2$ (3.1 g; 2.8 ml; 22 mmol) in methylene chloride (200 ml) at −10° C. After filtering the diazonium salt (water jet vacuum) at low temperature, it was suspended in THF (50 ml) at −20° C. and fed into a solution of phenol (20 mmol) (dissolve phenol in the minimum possible ethanol and add NaOH (10 g, 250 mmol) in 100 ml water) at −20° C. (stir for 1 h). The reaction mixture was then heated to 25° C. while stirring thoroughly and stirred for a further 15 h. To work up the solution, hexane was added and it was mixed thoroughly with dilute HCl, then washed with water to pH 7 and the aqueous phase was separated off. After drying the organic phase via $Na_2SO_4$, the dye was chromatographed through silica gel with hexane/methylene chloride=3/1 and can be purified further by crystallizing out of methanol at −20° C.

Transfer of the Acid Azo Dyes to the Corresponding Li Salt (Examples 1.1 to 1.2)

The azo dye (14.2 mmol) was dissolved in 150 ml tetrahydrofuran and cooled to −78° C. Diethyl ether can preferably also be used, if the azo dye is sufficiently soluble. n-BuLi (2.7 m in heptane; 5.8 ml, 15.6 mmol) was then added drop by drop and the reaction mixture is stirred for 1 h at −78° C. After heating to 25° C. the solvent was removed and 60 ml n-hexane is added. The purified product was obtained by crystallization at −20° C. and can immediately be processed further.

TABLE 1

Azo compounds

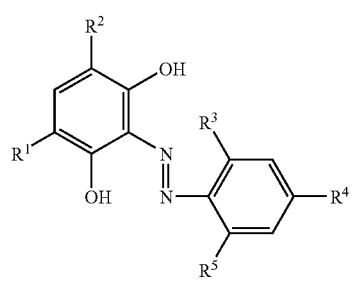

| Ex. | $R^1$ | $R^2$ | $R^3$ | $R^4$ | $R^5$ |
|---|---|---|---|---|---|
| 1.1 | tBu | tBu | Me | Me | Me |
| 1.2 | tBu | tBu | iPr | H | iPr |

TABLE 2

Lithium salts of the azo compounds

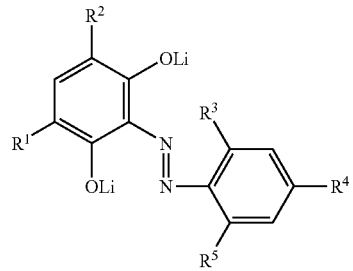

| Ex. | $R^1$ | $R^2$ | $R^3$ | $R^4$ | $R^5$ |
|---|---|---|---|---|---|
| 2.1 | tBu | tBu | Me | Me | Me |
| 2.2 | tBu | tBu | iPr | H | iPr |

Analytical data for compounds 1.1 to 1.2:

Azo Compounds:

Example 1.1

Anal. Rep. for $C_{23}H_{32}N_2O_2$ (368.51) C, 74.96; H, 8.75; N, 7.60; O, 8.68 found: C, 75.3; H, 8.8; N, 7.2. Smp.: 160° C. $^1$H-NMR in $CDCl_3$, [δ]: 1.42 (s, 18H, t-Bu), 2.35 (s, 3H, $CH_3$), 2.45 (s, 6H, $CH_3$), 6.99 (s, 2H, CH, Ar), 7.35 (s, 1H, CH, Ar). $^{13}C\{^1H\}$-NMR in $CDCl_3$, [δ]: 19.4 ($CH_3$, p-Me), 21.1 ($CH_3$, o-Me), 29.8 ($CH_3$, t-Bu), 34.5 (C, t-Bu), 127.0 (C, Ar) 127.9 (C, Ar), 130.2 (CH, Ar), 131.6 (CH, Ar), 131.7 (CH, Ar), 139.2 (C, Ar), 145.9 (C, Ar). IR: 1286 (m, $υ_{(N=N)}$), 3401 (S, $υ_{(OH,NH)}$).

Example 1.2

Anal. Rep. for $C_{26}H_{38}N_2O$ (394.59) C, 79.14; H, 9.71; N, 7.10; O, 4.05 found: C, 79.3; H, 9.6; N, 6.6. Smp.: 129° C. $^1$H-NMR in $CDCl_3$ [δ]: 1.22 (d, 6H, $^3J_{HH}$=6.9 Hz, $CH_3$, i-Pr), 1.43 (s, 18H, t-Bu), 3.09 (sp, 2H, $^3J_{HH}$=6.9 Hz, CH, i-Pr), 7.28 (d, 2H, $^3J_{HH}$=7.3 Hz, CH, Ar), 7.32 (t, 1H, $^3J_{HH}$=7.3 Hz, CH, Ar), 7.42 (s, 1H, CH, Ar), 8.0 (br, 1H, OH), 13.3 (br, 1H, OH). $^{13}C\{^1H\}$-NMR in $CDCl_3$ [ ]: 23.9 ($CH_3$, i-Pr), 27.9 (CH, i-Pr), 29.6 ($CH_3$, t-Bu), 34.5 (C, t-Bu), 123.8 (CH, Ar), 126.9 (C, Ar), 128.4 (CH, Ar), 132.5 (CH, Ar) 140.6 (C, Ar), 147.9 (C, Ar). IR: 1286 (m, $υ_{(N=N)}$), 3390 (s, $υ_{(OH, NH)}$).

Polymerization Examples

Nickel [Ni] Catalyst Mixture

The Li salt of the azo compound was dissolved in 1 ml toluene. 1 ml chlorobenzene was added to this solution. $Ni(COD)_2$ dissolved in 1 ml toluene was then added at −20° C. The solution obtained was heated to 25° C. and then used for polymerization.

General Procedure for Polymerization

Toluene, the polar additive, the activator and solution of the catalyst mixture, in that order, were fed through a canula into a 300 ml steel autoclave from which all impurities have been removed, fitted with a glass insert. The mixture was then stirred for 0.5 h at 30° C. and the ethylene pressure was then set to 8 bar. The polymerization time was 2 h and there was no temperature control for the exothermic reaction.

Once the reaction was complete, the reactor was de-pressurized and polymerization was terminated by adding a mixture of 5 ml each of isopropanol and methanol. The contents of the autoclave were poured into 300 ml methanol/HCl and the precipitated polymer was filtered and dried.

TABLE 3

Examples of polymerization

| Ex. No. | Total volume (ml) | Lig. | Lig. (mmol) | Activator | Activator (mmol) | Metal component [M] (mmol) | Additive | Additive (mmol) | Temp. (° C.) | Time (h) | Yield (g) |
|---|---|---|---|---|---|---|---|---|---|---|---|
| 3.1 | 43 | 1.2 | 0.065 | BF3/diethyl ether (1:1) | 0.129 | [Ni] (0.129) | — | — | 30/60 | 1 each | 0.5 |
| 3.2 | 43 | 1.2 | 0.065 | B(C6F5)3/diethyl ether (1:1) | 0.129 | [Ni] (0.129) | — | — | 30/60 | 1 each | 4.4 |
| 3.3 | 43 | 1.2 | 0.129 | B(C6F5)3/diethyl ether (1:1) | 0.129 | [Ni] (0.129) | — | — | 30/60 | 1 each | 3.85 |
| 3.4 | 43 | 1.2 | 0.043 | B(C6F5)3/diethyl ether (1:1) | 0.129 | [Ni] (0.043) | Acetonitrile | 4.3 | 30/60 | 1 each | 0 |

[Ni]: Ni(COD)$_2$, toluene, chlorobenzene, ethylene: 8 bar

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for the production of a catalyst comprising the steps
a) dissolution of compounds of the general formula (I)

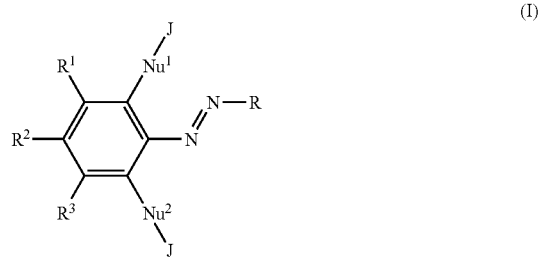

(I)

in a non-polar solvent, wherein
$Nu^1$, $Nu^2$ independently of each other stand for —O, —S, —Se, —PR$^a$, —NR$^a$, or —COO groups where R$^a$ is hydrogen, substituted or unsubstituted alkyl- or aryl groups and
J is an element selected from the 1$^{st}$ or 2$^{nd}$ main group of the periodic table
R, R$^1$, R$^2$ and R$^3$ are the same or different groups, which are selected independently of each other from the group consisting of H, halogens, substituted or unsubstituted C$_1$–C$_8$ alkyl-, C$_2$–C$_8$ alkenyl-, C$_3$–C$_{12}$ cycloalkyl-, C$_7$–C$_{13}$ aralkyl- and C$_6$–C$_{14}$ aryl groups and R$^1$ can form a ring with R$^2$ or R$^3$ and R$^2$ can form a ring with R$^3$;
b) dissolution of a metal compound of the general formula (II)

(II)

in a polar solvent, wherein
M stands for an element of the 4$^{th}$–12$^{th}$ sub-group of the periodic table,
L$^1$ is a neutral ligand,
L$^2$, L$^3$ are an anionic ligand, and L$^1$ and/or L$^2$ with L$^3$ can be linked to each other by one or more covalent bonds and
W can be an integer from 0 to 3,
Y can be an integer from 0 to 3 and
Z can be an integer from 0 to 3, wherein if one of the three variables W, Y or Z=0, the sum of the two remaining variables is equal to 2, 3 or 4;
c) mixing of solutions a) and b).

2. The process for the production of the catalyst according to claim 1, wherein
in formula (I)
Nu$^1$ and Nu$^2$ are —O,
J stands for an element of the 1$^{st}$ main group of the periodic table
R is selected from the group consisting of substituted or unsubstituted C$_6$–C$_{14}$ aralkyl groups
R$^1$, R$^2$ and R$^3$ are the same or different groups and are selected independently of each other from the group consisting of H, substituted or unsubstituted C$_1$–C$_8$ alkyl groups, C$_2$–C$_8$ alkenyl groups, C$_3$–C$_{12}$ cycloalkyl groups, C$_7$–C$_{13}$ aralkyl groups, and C$_6$–C$_{14}$ aryl groups
and in formula (II)
M is selected from the group consisting of Ti, Zr, Hf, Cr, V, Fe, Co, Ni, Ru, Rh, Pd, Os, Ir, Pt, Cu, Ag, Au, Zn, Cd and Hg
L$^1$ is an organic or inorganic neutral ligand selected from the group consisting of phosphanes of the general formula (R$^{13}$)$_x$PH$_{3-x}$, amines of the general formula (R$^{13}$)$_x$NH$_{3-x}$, tetraaralkyl ethylene diamines, ethers of the general formula (R$^{13}$)$_2$O, alcohols of the general formula (R$^{13}$)OH, pyridine derivatives of the general formula C$_5$H$_{5-x}$(R$^{13}$)$_x$N, CO, C$_1$–C$_{12}$ alkyl nitrile, C$_6$–C$_{14}$ aryl nitrile and mono- or polyethylenically unsaturated double bond systems, wherein
R$^{13}$ is selected from the group consisting of H, C$_1$–C$_8$ alkyl groups, benzyl groups and C$_6$–C$_{14}$ aryl groups and
x stands for an integer from 0 to 3, and
L$^2$, L$^3$ is an anionic ligand selected from the group consisting of halide ions, amide anions of the formula R$^{14}$R$^{15}$N, C$_1$–C$_6$-alkyl anions, allyl anions, methallyl anions, benzyl anions and aryl anions, wherein R$^{14}$ and R$^{15}$ are selected independently of each other from the group consisting of H, C$_1$–C$_8$ alkyl groups, benzyl groups and C$_6$–C$_{14}$ aryl groups and R$^{14}$ can also be covalently linked to R$^{15}$ and W is an integer from 0 to 3

Y is an integer from 0 to 3 and

Z can be an integer from 0 to 3, wherein if one of the three variables W, Y or Z=0, the sum of the two remaining variables is equal to 2, 3 or 4.

3. The process for the production of the catalyst according to claim 1, wherein in formula (I)

Nu$^1$ and Nu$^2$ are O,

J is lithium or hydrogen

R is mesityl, 2,4,6-trimethylphenyl or 2,6-diisopropylphenyl,

R$^1$, R$^2$ and R$^3$ are the same or different groups and are selected independently of each other from the group consisting of H, C$_1$–C$_8$ alkyl groups and C$_6$–C$_{14}$ aryl groups and in formula II M is selected from the group consisting of Ti, Zr, Cr, V, Fe, Co, Ni, Pd, Cu and Zn L$^1$ is a neutral ligand, selected from the group consisting of triphenyl phosphine, triethyl phosphine, trimethyl phosphine, trimethyl phosphane, dibenzo phosphol, triphenyl phosphite, triethyl phosphite, trimethyl phosphite, triphenyl phosphite, trimethyl amine, triethyl amine, dimethyl aniline, diethyl aniline, benzyl dimethyl amine, benzyl diethyl amine, diisopropyl amine, diethyl amine, dimethyl amine, diphenyl amine, phenylene diamine, tetramethyl ethylene diamine, diethyl ether, tetrahydrofuran, water, methanol, ethanol, pyridine, 2-picoline, 3-picoline, 4-picoline, 2,3-lutidine, 2,4-lutidine, 2,5-lutidine, 2,6-lutidine, 3,5-lutidine, CO, acrylonitrile, propionitrile, butyronitrile, benzonitrile, ethenyl, propenyl, cis-2-butenyl, trans-2-butenyl, cyclohexenyl, norbornenyl, and 1,5-cyclooctadiene L$^2$, L$^3$ is an anionic ligand selected from the group consisting of chloride, bromide, dimethyl amide, diethyl amide, amide, 2-carboxylic acid ester metallyl, allyl, methyl, ethyl, n-propyl, i-propyl, n-butyl, tert-butyl, hexyl and phenyl, W is an integer from 0 to 3

Y is an integer from 0 to 3

Z can be an integer from 0 to 3, wherein if one of the three variables W, Y or Z=0, the sum of the two remaining variables is equal to 2,3 or4.

4. The process for the production of the catalyst according to claim 1, wherein in formula (I)

Nu$^1$ and Nu$^2$ are —O,

J is hydrogen or lithium

R is mesityl or 2,6-diisopropyl phenyl

R$^1$ is tert-butyl

R$^2$ is H

R$^3$ is tert-butyl in formula (II)

M is Ni or Pd

L$^1$ is tetramethylene diamine, triphenyl phosphane, trimethyl phosphane or 1,5-cyclooctadiene L$^2$, L$^3$ are chloride, phenyl or methyl and W is 1 or 2

Y is 1 or 2 and

Z is 1 or 2.

5. A catalyst prepared by a) dissolution of compounds of the general formula (I)

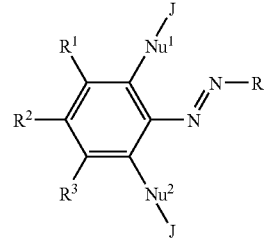

(I)

in a non-polar solvent, wherein

Nu$^1$, Nu$^2$ independently of each other stand for —O, —S, —Se, —PR$^a$, —NR$^a$, or —COO groups where R$^a$ is hydrogen, substituted or unsubstituted alkyl- or aryl groups and J is an element selected from the 1$^{st}$ or 2$^{nd}$ main group of the periodic table R, R$^1$, R$^2$ and R$^3$ are the same or different groups, which are selected independently of each other from the group consisting of H, halogens, substituted or unsubstituted C$_1$–C$_8$ alkyl-, C$_2$–C$_8$ alkenyl-, C$_3$–C$_{12}$ cycloalkyl-, C$_7$–C$_{13}$ aralkyl- and C$_6$–C$_{14}$ aryl groups and R$^1$ can form a ring with R$^2$ or R$^3$ and R$^2$ can form a ring with R$^3$;

b) dissolution of a metal compound of the general formula (II)

$$M(L^1)_W(L^2)_Y(L^3)_Z \quad (II)$$

in a polar solvent, wherein

M stands for an element of the 4$^{th}$–12$^{th}$ sub-group of the periodic table, L$^1$ is a neutral ligand, L$^2$, L$^3$ are an anionic ligand, and L$^1$ and/or L$^2$ with L$^3$ can be linked to each other by one or more covalent bonds and W can be an integer from 0 to 3, Y can be an integer from 0 to 3 and Z can be an integer from 0 to 3, wherein if one of the three variables W, Y or Z=0, the sum of the two remaining variables is equal to 2, 3 or 4;

c) mixing of solutions a) and b).

6. Process for the production of olefin (co)polymers comprising reacting the catalyst according to claim 5 in the presence of olefinic monomers selected from the group consisting of 1-olefins, cycloolefins, functionalized 1-olefins and mixtures thereof.

7. Process according to claim 6, wherein boron or aluminum compounds are added as co-catalysts to the reaction mixture.

8. Process according to claim 7, wherein the molar ratio of co-catalyst to metal M in the compound of formula (II) is in the range of 1:10 to 1:10000.

9. Process according to claim 6, wherein aluminum oxanes are used as co-catalysts.

10. Process according to claim 6, wherein polymerization is carried out in polar solvents or solvent mixtures.

11. Reaction products produced by reacting the catalyst according to claim 1 with a co-catalyst(s).

* * * * *